United States Patent
Haws et al.

(10) Patent No.: US 9,483,739 B2
(45) Date of Patent: *Nov. 1, 2016

(54) TRANSDUCTIVE FEATURE SELECTION WITH MAXIMUM-RELEVANCY AND MINIMUM-REDUNDANCY CRITERIA

(71) Applicant: International Business Machines Corporation, Armonk, NY (US)

(72) Inventors: David Haws, New York, NY (US); Dan He, Ossining, NY (US); Laxmi P. Parida, Mohegan Lake, NY (US); Irina Rish, Rye Brook, NY (US)

(73) Assignee: International Business Machines Corporation, Armonk, NY (US)

( * ) Notice: Subject to any disclaimer, the term of this patent is extended or adjusted under 35 U.S.C. 154(b) by 535 days.

This patent is subject to a terminal disclaimer.

(21) Appl. No.: 14/030,708

(22) Filed: Sep. 18, 2013

(65) Prior Publication Data

US 2014/0207713 A1    Jul. 24, 2014

Related U.S. Application Data

(63) Continuation of application No. 13/745,930, filed on Jan. 21, 2013.

(51) Int. Cl.
*G06F 15/18* (2006.01)
*G06N 99/00* (2010.01)
(Continued)

(52) U.S. Cl.
CPC .............. *G06N 99/005* (2013.01); *G06F 17/18* (2013.01); *G06K 9/6231* (2013.01); *G06F 19/24* (2013.01); *G06K 9/6256* (2013.01); *G06N 5/025* (2013.01); *G06N 7/005* (2013.01)

(58) Field of Classification Search
None
See application file for complete search history.

(56) References Cited

U.S. PATENT DOCUMENTS 7,421,417 B2   9/2008   Mangasarian et al.
7,500,216 B1   3/2009   Blunno et al.
(Continued)

FOREIGN PATENT DOCUMENTS

WO    2012097152    7/2012

OTHER PUBLICATIONS

Feature Selection Based on Mutual Information: Criteria of Max-Dependency, Max-Relevance, and Min-Redundancy Hanchuan Peng, Member, IEEE, Fuhui Long, and Chris Ding IEEE Transactions on Pattern Analysis and Machine Intelligence, vol. 27, No. 8, Aug. 2005.*

(Continued)

*Primary Examiner* — Kakali Chaki
*Assistant Examiner* — Ababacar Seck
(74) *Attorney, Agent, or Firm* — Fleit Gibbons Gutman Bongini Bianco PL; Thomas S. Grzesik

(57) ABSTRACT

Various embodiments select features from a feature space. In one embodiment, a set of training samples and a set of test samples are received. The set of training samples includes a set of features and a class value. The set of test samples includes the set of features absent the class value. A relevancy with respect to the class value is determined for each of a plurality of unselected features based on the set of training samples. A redundancy with respect to one or more of the set of features is determined for each of the plurality of unselected features in the first set of features based on the set of training samples and the set of test samples. A set of features is selected from the plurality of unselected features based on the relevancy and the redundancy determined for each of the plurality of unselected features.

12 Claims, 2 Drawing Sheets

(51) Int. Cl.
G06F 17/18 (2006.01)
G06N 7/00 (2006.01)
G06N 5/02 (2006.01)
G06K 9/62 (2006.01)
G06F 19/24 (2011.01)

(56) References Cited

U.S. PATENT DOCUMENTS

| | | | |
|---|---|---|---|
| 7,624,074 | B2 | 11/2009 | Weston et al. |
| 2006/0253427 | A1* | 11/2006 | Wu .................... G06F 17/3064 |
| 2007/0122001 | A1 | 5/2007 | Wang et al. |
| 2007/0168306 | A1 | 7/2007 | Li et al. |
| 2007/0216675 | A1 | 9/2007 | Sun et al. |
| 2010/0082513 | A1 | 4/2010 | Liu |
| 2010/0287093 | A1 | 11/2010 | He et al. |
| 2010/0332430 | A1 | 12/2010 | Caraviello et al. |
| 2011/0038515 | A1 | 2/2011 | Jacquin et al. |
| 2011/0072130 | A1 | 3/2011 | Jiang et al. |
| 2011/0246409 | A1 | 10/2011 | Mitra |
| 2011/0307437 | A1 | 12/2011 | Aliferis et al. |
| 2012/0088981 | A1 | 4/2012 | Liu et al. |
| 2012/0177280 | A1 | 7/2012 | Zhukov et al. |
| 2012/0290607 | A1 | 11/2012 | Bhargava et al. |
| 2012/0310863 | A1 | 12/2012 | Crockett et al. |
| 2013/0109995 | A1 | 5/2013 | Rothman et al. |
| 2013/0150257 | A1 | 6/2013 | Abdueva et al. |
| 2013/0184603 | A1 | 7/2013 | Rothman |
| 2013/0231258 | A1 | 9/2013 | Wilde et al. |
| 2014/0064581 | A1 | 3/2014 | Madabhushi et al. |
| 2014/0278981 | A1 | 9/2014 | Mersov et al. |

OTHER PUBLICATIONS

Non-Final Office Action dated Oct. 1, 2015 received for U.S. Appl. No. 13/745,914.
Gayan, J., et al., "A Method for Detecting Epistasis in Genome-wide Studies Using Case-control Multi-locus Association Analysis", BMC Genomics, Jul. 2008, pp. 1-14.
Zhang, L., et al., "Modeling Haplotype-haplotype Interactions in Case-Control Genetic Association Studies", Frontiers in Genetics, Jan. 2012, pp. 1-18, vol. 3, Article 2.
Andreasen, N.C., et al., "Statistical Epistasis and Progressive Brain Change in Schizophrenia: An Approach for Examining the Relationships Between Multiple Genes", Molecular Psychiatry, Nov. 2012, pp. 1-19.
Non-Final Office Action dated Feb. 1, 2016 received for U.S. Appl. No. 14/030,806.
Non-Final Office Action dated Jul. 7, 2014, received for U.S. Appl. No. 13/745,923.
Non-Final Office Action dated Dec. 12, 2014, received for U.S. Appl. No. 14/030,720.
Non-Final Office Action dated Jul. 3, 2014, received for U.S. Appl. No. 13/745,909.
Non-Final Office Action dated Dec. 16, 2014, received for U.S. Appl. No. 14/030,806.
Zhisong H., et al., "Prediciting Drug-Target Interaction Networks Based on Functional Groups and Biological Features," PLos One, Mar. 2010, pp. 1-8, vol. 5 Issue 3.
Kachel, A., et al., "Infosel++: Information Based Feature Selection C++ Library," 10th International Conference: Artificial Intelligence and Soft Computing, Jun. 2010, pp. 1-9.
Liu, H., "Evolving Feature Selection," Trends and Controversies, Nov. and Dec. 2005, pp. 1-13.
Zhisong, H., et al., "Computational Analysis of Protein Tyrosine Nitration," The Fourth International Conference on Computational Systems Biology, Sep. 9-11, 2010, pp. 1-8.
Premebida, C., et al., "Exploiting LIDAR-based features on Pedestrian Detection in Urban Scenarios," Proceedings of the 12th International IEEE Conference on Intelligent Transportation Systems, Oct. 3-7, 2009, pp. 1-6.

Mundra, P., et al., "SVM-RFE With MRMR Filter for Gene Selection," IEEE Transactions on Nanobioscience, Mar. 2010, pp. 1-7. vol. 7, Issue 1.
Liu, H., et al., "Feature Selection with dynamic mutual information," Pattern Recognition, Oct. 2008, pp. 1-10, vol. 42.
Estevez, P., et al., "Normalized Mutual Information Feature Selection," IEEE Transactions on Neural Networks, Feb. 2009, pp. 1-13. vol. 20, Issue 02.
Dong, D., et al., "Gene Expression Variations Are Predictive for Stochastic Noise," Nucleic Acids Research, Sep. 21, 2011, pp. 1-12, vol. 39, Issue 02.
Jiang, X., et al., "Mining Pure, Strict Epistatic Interactions from High-Dimensional Datasets: Ameliorating the Curse of Dimensionality," PLoS one, Oct. 2012, pp. 1-12, vol. 7, Issue 10.
Zhang, Z. et al, "MRMR Optimized Classification for Automatic Glaucoma Diagnosis", 33rd Annual Conference of the IEEE, EMBS, Aug. 30-Sep. 3, 2011, pp. 6228-6231.
Non Final Office Action dated Jan. 15, 2015, received for U.S. Appl. No. 13/745,930.
Final Office Action dated May 15, 2015, received for U.S. Appl. No. 14/030,720.
Yang, Y., et al., "Recursive Feature Selection Based on Minimum Redundancy Maximum Relevancy", PAAP, Dec. 18-10, 2010, pp. 281-285.
Yang, X., et al., "Feature Selection for Computer-Aided Polyp Detection using MRMR," SPIE 7624, Medical Imaging, Feb. 13, 2010, pp. 1-8.
Zhu, S., et al., "Feature Selection for Gene Expression Using Model-Based Entropy", IEEE/ACM Transactions on Computational Biology and Bioinformatics, Jan.-Mar. 2010, pp. 25-36, vol. 7, No. 1.
Luo, D., et al., "SOR: Scalable Orthogonal Regression for Non-Redundant Feature Selection and its Healthcare Applications", SIAM data mining conference, Apr. 26-28, 2012, pp. 576-587.
Final Office Action dated May 22, 2015, received for U.S. Appl. No. 14/030,806.
Meyer, P., et al., "Information-Theoretic Feature Selection in Microarray Data Using Variable Complementarity," IEEE Journal of Selected Topics on Signal Processing, Jun. 2008, pp. 261-274, vol. 2, No. 3.
Liu, F., et al., "A Novel Ordering-Based Greedy Bayesian Network Learning Algorithm on Limited Data", Advances in Artificial Intelligences, Oct. 2007, pp. 80-89.
Li, J., et al., "Chap. 5: Identification of Marker Genes from High-Dimensional Microarray Data for Cancer Classification", Knowledge Discovery in Bioinformatics: Techniques, Methods, and Applications, May 2007, pp. 71-87.
El-Akadi, A., et al., "A New Gene Selection Approach Based on Minimum Redundancy-Maximum Relevance (MRMR) and Genetic Algorithm (GA)", May 10-13, 2009, pp. 69-75.
Nugraha, I., et al., "Performance Analysis of Relief and mRMR Algorithm Combination for Selecting Features in Lupus Genome-Wide Association Study," International Conference on Electrical Engineering and Informatics, Jul. 17-19, 2011, pp. 1-5.
Yu, D., et al., "Fuzzy Mutual Information Based min-Redundancy and Max-Relevance Heterogenous Feature Selection," International Journal of Computational Intelligence Systems, Jun. 2011, pp. 619-633. vol. 4, No. 4.
El-Akadi, A., "A two-stage gene selection scheme utilizing MRMR filter and GA wrapper", Knowledge and Information Systems, Mar. 2011, pp. 487-500, vol. 26, Issue 3.
Zelenak, M., et al., "Speaker overlap detection with prosodic features for speaker diarisation," IET Processing, Oct. 16, 2012, pp. 798-804, vol. 6, Issue 8.
Wikipedia., "Feature Selection," Downloaded on Mar. 26, 2015, pp. 1-16.
Wikipedia., "Hill Climbing," Downloaded Mar. 26, 2015, pp. 1-5.
Wikipedia., "Minimum redundancy feature selection," Downloaded Mar. 26, 2015, pp. 1-2.
Final Office Action dated Aug. 12, 2015 received for U.S. Appl. No. 13/745,930.

(56) References Cited

OTHER PUBLICATIONS

Alquier, P., "LASSO, Iterative Feature Selection and the Correlation Selector: Oracle Inequalities and Numerical Performances." Electronic Journal of Statistics, 2:1129-1152, Aug. 2008, ISSN:1935-7524, DOI: 10.1214/08-EJS288.
Cai, Y. et al., "Prediction of Protein Subcellular Locationswith Feature Selection and Analysis." Protein and Peptide Letters, 17(4):464-472, 2010, PLoS One. 2012; 7(6):e39308, published online Jun. 15, 2012. doi: 10.1371/journal.pone.0039308.
Cortes, C. et al., "On transductive regression." Advances in Neural Information Processing Systems, 19:305,2007.
Dash, M. et al., "Feature selection for classification," Intelligent Data Analysis, 1(1-4):131-156, Mar. 1997, 1088-467x/97, copyright 1997.
Ding, C. et al., "Minimum redundancy feature selection from microarray gene expression data." In Bioin-formatics Conference, 2003. CSB 2003. Proceedings of the 2003 IEEE, pp. 523-528. IEEE, Oct. 2003, Journal of Bioformatics and Computational Biology, vol. 3, No. 2 (2005) 185-205, Imperial College Press.
Guyon, I. et al., "An introduction to variable and feature selection. The Journal of Machine Learning Research", 3:1157-1182, Mar. 2003.
Jain, A. et al., "Feature selection: Evaluation, application, and small sample performance," Pattern Analysis and Machine Intelligence, IEEE Transactions on, 19(2):153-158 Feb. 1997.
Peng, H. et al., "Feature selection based on mutual information criteria of max-dependency, max-relevance, and min-redundancy". Pattern Analysis and Machine Intelligence, IEEE Transactions on, 27(8):1226-1238, Aug. 2005. 0162-8828/05 copyright.
Zhang, Y. et al., "Gene selection algorithm by combining relieff and mrmr." BMC genomics, 9(Suppl 2):S27, Sep. 2008. IEEE 7th International Conference in Bioformatics and Bioengineering at Harvard Medical School.
Skalak, David B., "Prototype and feature selection by sampling and random mutation hill climbing algorithms," In Proceedings of the eleventh international conference on machine learning, pp. 293-301, 1994.
Vafaie, H. et al., "Robust feature selection algorithms," In Tools with Artificial Intelligence, TAI'93, Proceedings., Fifth International Conference , pp. 356-363, IEEE, Nov. 1993.
Tsamardinos, I. et al., "The max-min hill-climbing Bayesian network structure learning algorithm," Machine learning, 65.1: 31-78. Mar. 2006. DOI 10.1007/s10994-006-6889-7.
Gammerman, A. et al., "Learning by transduction". In Proceedings of the Fourteenth Conference on Uncertainty in Artificial Intelligence, pp. 148-155. Morgan Kaufmann Publishers Inc., 1998.
Yang, Y. et al., "A comparative study on feature selection in text categorization" . In machine learning-International workshop , pp. 412-420. Morgan Kauf-mann publishers, Inc., 1997.
Farmer, M.E. et al., "Large scale feature selection using modified random mutation hill climbing," In Pattern Recognition, 2004, ICPR 2004, Proceedings of the 17th International Conference on Pattern Recognition, vol. 2, pp. 287-290, IEEE, Aug. 2004.
Haung, T. et al., "Analysis and Prediction of the Metabolic Stability of Proteins Based on Their Sequential Features, Subcellular Locations and Interaction Networks". Jun. 4, 2010. PLoS ONE 5(6): e10972. doi:10.1371/journal.pone.0010972. Copyright 2010.
J.R. Kilpatrick, "Methods for detecting multi-locus genotype-phenotype association", pp. 1-152, PhD thesis, Rice University, 2009.
Final Office Action dated Nov. 19, 2015 received for U.S. Appl. No. 14/030,720.
Vinh, L., et al., "A Novel Feature Selection Method Based on Normalized Mutual Information", Applied Intelligence, Aug. 23, 2011, pp. 1-21, vol. 37, Issue 1.
Zhao, Z., et al., "Advancing Feature Selection Research", ASU Feature Selection Repository, 2010, pp. 1-28.
Final Office Action dated Nov. 17, 2015 received for U.S. Appl. No. 13/745,930.
Final Office Action dated Mar. 18, 2016, received for U.S. Appl. No. 13/745,914.
Ma, L., et al., "Parallel and serial computing tools for testing single-locus and epistatic SNP effects of quantitative traits in genome-wide association studies", BMC Bioinformatics, Jul. 21, 2008, pp. 1-9, vol. 9, No. 1.

* cited by examiner

US 9,483,739 B2

TRANSDUCTIVE FEATURE SELECTION WITH MAXIMUM-RELEVANCY AND MINIMUM-REDUNDANCY CRITERIA

CROSS-REFERENCE TO RELATED APPLICATIONS

This application is based upon and claims priority from prior U.S. patent application Ser. No. 13/745,930, filed on Jan. 21, 2013, the entire disclosure of which is herein incorporated by reference in its entirety.

BACKGROUND

The present invention generally relates to the field of feature selection, and more particularly relates to transductive feature selection based on Max-Relevancy and Min-Redundancy criteria.

Feature selection methods are critical for classification and regression problems. For example, it is common in large-scale learning applications, especially for biology data such as gene expression data and genotype data, that the amount of variables far exceeds the number of samples. The "curse of dimensionality" problem not only affects the computational efficiency of the learning algorithms, but also leads to poor performance of these algorithms. To address this problem, various feature selection methods can be utilized where a subset of important features is selected and the learning algorithms are trained on these features.

BRIEF SUMMARY

In one embodiment, a computer implemented method for selecting features from a feature space is disclosed. The method includes receiving a set of training samples and a set of test samples. The set of training samples includes a first set of features and a class value. The set of test samples includes the set of features absent the class value. A relevancy with respect to the class value is determined for each of a plurality of unselected features in the set of features based on the set of training samples. A redundancy with respect to the set of features is determined for each of the plurality of unselected features based on the set of training samples and the set of test samples. A set of features is selected from the plurality of unselected features based on the relevancy and the redundancy determined for each of the plurality of unselected features.

In one embodiment, an information processing system for selecting features from a feature space is disclosed. The information processing system includes a memory and a processor that is communicatively coupled to the memory. A feature selection module is communicatively coupled to the memory and the processor. The feature selection module is configured to perform a method. The method includes receiving a set of training samples and a set of test samples. The set of training samples includes a first set of features and a class value. The set of test samples includes the set of features absent the class value. A relevancy with respect to the class value is determined for each of a plurality of unselected features in the set of features based on the set of training samples. A redundancy with respect to the set of features is determined for each of the plurality of unselected features based on the set of training samples and the set of test samples. A set of features is selected from the plurality of unselected features based on the relevancy and the redundancy determined for each of the plurality of unselected features.

In one embodiment, a non-transitory computer program product for selecting features from a feature space is disclosed. The computer program product includes a storage medium readable by a processing circuit and storing instructions for execution by the processing circuit for performing a method. The method includes receiving a set of training samples and a set of test samples. The set of training samples includes a first set of features and a class value. The set of test samples includes the set of features absent the class value. A relevancy with respect to the class value is determined for each of a plurality of unselected features in the set of features based on the set of training samples. A redundancy with respect to the set of features is determined for each of the plurality of unselected features based on the set of training samples and the set of test samples. A set of features is selected from the plurality of unselected features based on the relevancy and the redundancy determined for each of the plurality of unselected features.

BRIEF DESCRIPTION OF THE SEVERAL VIEWS OF THE DRAWINGS

The accompanying figures where like reference numerals refer to identical or functionally similar elements throughout the separate views, and which together with the detailed description below are incorporated in and form part of the specification, serve to further illustrate various embodiments and to explain various principles and advantages all in accordance with the present invention, in which.

DETAILED DESCRIPTION

Figure 1:
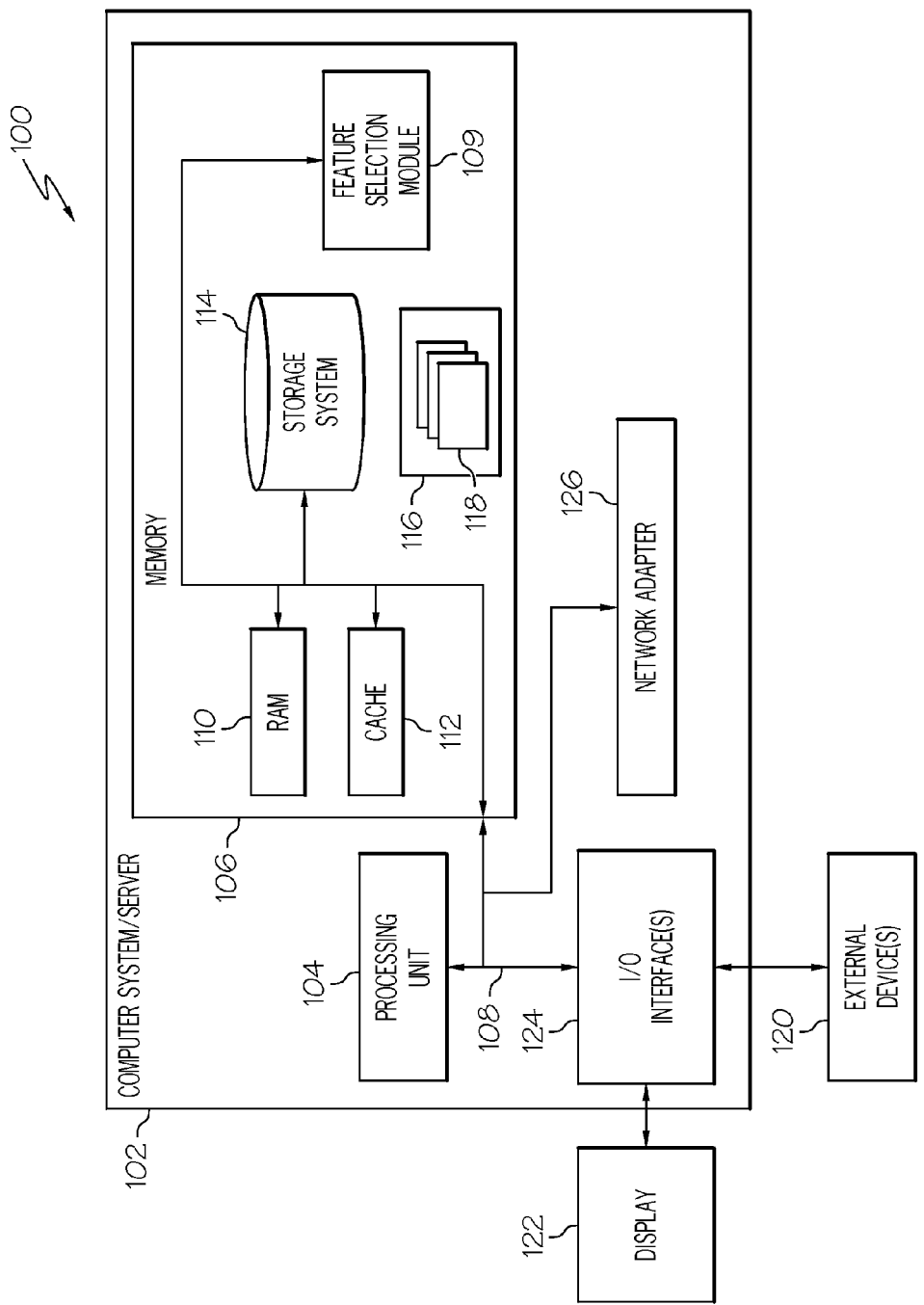
FIG. 1 is a block diagram illustrating one example of an operating environment according to one embodiment of the present invention.

FIG. 1 illustrates a general overview of one operating environment 100 for generating quantitative models of multi-allelic multi-loci interactions for genetic simulation and prediction problems according to one embodiment of the present invention. In particular, FIG. 1 illustrates an information processing system 102 that can be utilized in embodiments of the present invention. The information processing system 102 shown in FIG. 1 is only one example of a suitable system and is not intended to limit the scope of use or functionality of embodiments of the present invention described above. The information processing system 102 of FIG. 1 is capable of implementing and/or performing any of the functionality set forth above. Any suitably configured processing system can be used as the information processing system 102 in embodiments of the present invention.

As illustrated in FIG. 1, the information processing system 102 is in the form of a general-purpose computing device. The components of the information processing system 102 can include, but are not limited to, one or more processors or processing units 104, a system memory 106, and a bus 108 that couples various system components including the system memory 106 to the processor 104.

The bus 108 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The system memory 106, in one embodiment, includes a feature selection module 109 configured to perform one or more embodiments discussed below. For example, in one embodiment, the feature selection 109 is configured to perform transductive Max-Relevance and Min-Redundancy (MRMR) feature selection operations, which are discussed in greater detail below. It should be noted that even though FIG. 1 shows the feature selection module 109 residing in the main memory, the feature selection module 109 can reside within the processor 104, be a separate hardware component capable of e, and/or be distributed across a plurality of information processing systems and/or processors.

The system memory 106 can also include computer system readable media in the form of volatile memory, such as random access memory (RAM) 110 and/or cache memory 112. The information processing system 102 can further include other removable/non-removable, volatile/non-volatile computer system storage media. By way of example only, a storage system 114 can be provided for reading from and writing to a non-removable or removable, non-volatile media such as one or more solid state disks and/or magnetic media (typically called a "hard drive"). A magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 108 by one or more data media interfaces. The memory 106 can include at least one program product having a set of program modules that are configured to carry out the functions of an embodiment of the present invention.

Program/utility 116, having a set of program modules 118, may be stored in memory 106 by way of example, and not limitation, as well as an operating system, one or more application programs, other program modules, and program data. Each of the operating system, one or more application programs, other program modules, and program data or some combination thereof, may include an implementation of a networking environment. Program modules 118 generally carry out the functions and/or methodologies of embodiments of the present invention.

The information processing system 102 can also communicate with one or more external devices 120 such as a keyboard, a pointing device, a display 122, etc.; one or more devices that enable a user to interact with the information processing system 102; and/or any devices (e.g., network card, modem, etc.) that enable computer system/server 102 to communicate with one or more other computing devices. Such communication can occur via I/O interfaces 124. Still yet, the information processing system 102 can communicate with one or more networks such as a local area network (LAN), a general wide area network (WAN), and/or a public network (e.g., the Internet) via network adapter 126. As depicted, the network adapter 126 communicates with the other components of information processing system 102 via the bus 108. Other hardware and/or software components can also be used in conjunction with the information processing system 102. Examples include, but are not limited to: microcode, device drivers, redundant processing units, external disk drive arrays, RAID systems, tape drives, and data archival storage systems.

One criterion for feature selection is referred to as Maximum-Relevance and Minimum-Redundancy (MRMR). In MRMR the selected features should be maximally relevant to the class value, and also minimally dependent on each other. In MRMR, the Maximum-Relevance criterion searches for features that maximize the mean value of all mutual information values between individual features and a class variable. However, feature selection based only on Maximum-Relevance tends to select features that have high redundancy, namely the correlation of the selected features tends to be high. If some of these highly correlated features are removed the respective class-discriminative power would not change, or would only change by an insignificant amount. Therefore, the Minimum-Redundancy criterion is utilized to select mutually exclusive features. A more detailed discussion on MRMR is given in Peng et al., "Feature selection based on mutual information criteria of max-dependency, max-relevance, and min-redundancy", Pattern Analysis and Machine Intelligence, IEEE Transactions on, 27(8): 1226-1238, 2005, which is hereby incorporated by reference in its entirety.

Transduction assumes a setting where test data points are available to the learning algorithms. Therefore the learning algorithms can be more specific in that they can learn not only from the training data set, but also from the test data set. However, a challenge exists in determining how to utilize the test data points in the most useful way. For example, one usually only has access to the features of the test data points is, and not their class values. Therefore, it is generally difficult for one to integrate these features from the test data points into the learning algorithms. A general solution is imputation where the missing class values of the test data points are imputed by the model that is learned on the training data set only. Another type of imputation computes the missing class values of the test data points using their closest neighbors in the training data set. These imputation strategies, however, may not work well when the dimensionality of the data set is very high which usually leads to poor imputations. Therefore, it is very challenging to determine how to utilize the test data points in the most useful way.

However, one or more embodiments provide a transductive feature selection method, referred to here as (TMRMR), that utilizes the criteria of MRMR to transductively select features from a feature space that includes training data and test data. In one embodiment, training data is the set of data where the target values are available. In this embodiment, test data is the set of data where the target values are missing and to be predicted. The criteria of MRMR can be separated into two independent components, one for maximum relevance and one for minimum redundancy. Maximum relevance requires calculation of the mutual information (or correlation) between the selected features and the class value. During the Maximum Relevance selection process of TMRMR only training data features are considered since the class value of the test samples is not available. Minimum Redundancy, on the other hand, calculates the mutual information among all the selected features and the class value is not involved. Therefore, during the Minimum Redundancy of the TMRMR method all training sample and test samples are considered, which provides a transductive learning mechanism.

In particular, the feature selection module 109 receives as input a set of training samples, each including a set of features ($x^{training}$) and a class/target value c. The feature selection module 109 also receives a set of test samples, each including only the same set of features ($x^{test}$) as the training samples with target values missing. The number of features to be selected is also received as input by the feature selection module 109. In one embodiment, features can be represented as rows and samples as columns. Therefore, the training and test samples comprise the same columns (features), but different rows (samples).

The feature selection module 109 maintains two pools of features, one pool for selected features (referred to herein as the "SF pool"), and one pool for the remaining unselected features (referred to herein as the "UF pool"). The UF pool initially includes all the features from the training and test samples, while the SF pool is initially empty. In this embodiment, features are incrementally selected from the feature set S in a greedy way while simultaneously optimizing the following Maximum-Relevancy and Minimum-Redundancy conditions:

$$\max D(S, c), \quad D = \frac{1}{|S|} \sum_{x_i \in S} I(x_j^{training}; c^{training}) \quad \text{(EQ 1)}$$

$$\min R(S), \quad R = \frac{1}{|S|^2} \sum_{x_i, x_j \in S} I(x_j^{training+test}; x_i^{training+test}). \quad \text{(EQ 2)}$$

For example, the feature selection module 109 performs a TMRMR selection process that optimizes EQ 1 and EQ 2 above. The TMRMR selection process transductively selects a set of features from the feature space that includes training data and test data according to:

$$\max_{x_j \in X-S_{m-1}} \left[ I(x_j^{training}; c^{training}) - \frac{1}{m-1} \sum_{x_i \in S_{m-1}} I(x_j^{training+test}; x_i^{training+test}) \right], \quad \text{(EQ 3)}$$

where $x_j$ is the jth feature that is sample independent, $x_j^{training}$ is the jth feature from a training sample, $x_j^{training+test}$ is the jth feature from the training and test samples, i is an integer, X is the set of all original input features, $S_{m-1}$ is a set of m−1 features, c is the class value associated with the training data set, and I is mutual information.

Features are selected in an incremental fashion according to EQ 3, where previously selected features (if any) remain in the feature set S, but are not selected. For example, if m features have already been selected for the set S, the set S is now includes m−1 features. The task is to select the mth feature from the set $\{X-S_{m-1}\}$, where X is all of the features (i.e., the input set of features). In this embodiment, when calculating relevancy of features, the feature selection module 109 only considers candidate features from the training samples. The feature selection module 109 identifies a feature that maximizes the relevance of the feature to the class value. For example, each feature $x_j^{training}$ selected from the training samples has the largest mutual information $I(x_j^{training}; c^{training})$ with the target class $c^{training}$, where mutual information I of two variables x and y can be defined, based on their joint marginal probabilities p(x) and p(y) and probabilistic distribution p(x, y), as:

$$I(x, y) = \sum_{i,j} p(x_i, y_i) \log \frac{p(x_i, y_i)}{p(x_i)p(y_i)}. \quad \text{(EQ 4)}$$

It should be noted that other method for determining the mutual information I of variables can also be used.

Selecting features based on Max-Relevancy can lead to subsets of redundant or highly correlated features. Therefore, in addition to selecting features based on Max-Relevancy the feature selection module 109 also considers Minimum-Redundancy when selecting a feature. When calculating redundancy the feature selection model considers features from the training samples and the test samples. Therefore, each selected feature maximizes the relevance of the feature to the target value, considering only the training samples, and also minimizes the redundancy of the feature with all the selected features in the SF pool, considering both the training and test samples. Based on the above, the selection feature module 109 outputs a subset features that is used to build a model to predict the missing target values of the test samples.

It should be noted that since the TMRMR process discussed above is test data specific, the feature selection model would normally need to be re-trained every time for new test data points. However, in one embodiment, retraining the model from scratch can be avoided. For example, TMRMR includes two components, one for relevance and one for redundancy. Since redundancy is between the features, the feature selection module 109 pre-saves the counts for the values of the features that are used to compute the mutual information I between features for the training data. When the test data points arrived, the feature selection module updates these counts by considering the test data points. Thus, the training of the model is incremental rather than from scratch. Therefore, TMRMR is not only more accurate than conventional MRMR methods, but can also improve MRMR feature selection methods.

Furthermore, the performance of TMRMR is relevant to the entropy of the target values. In some embodiment TMRMR rounds the target values to compute mutual information. Therefore, when the target values are very small, e.g., close to each other within a threshold or close to 0 within a threshold, the rounded target values have very different entropy compared with the original target values. This phenomenon usually leads to poor performance. Therefore, in on embodiment, the feature selection module 109 multiplies the target values by a scalar such that the entropy of the rounded target values after scaling is almost identical (e.g., within a given threshold) to the entropy of the original target values. Thus, the information from the target values can be retained.

Figure 2:
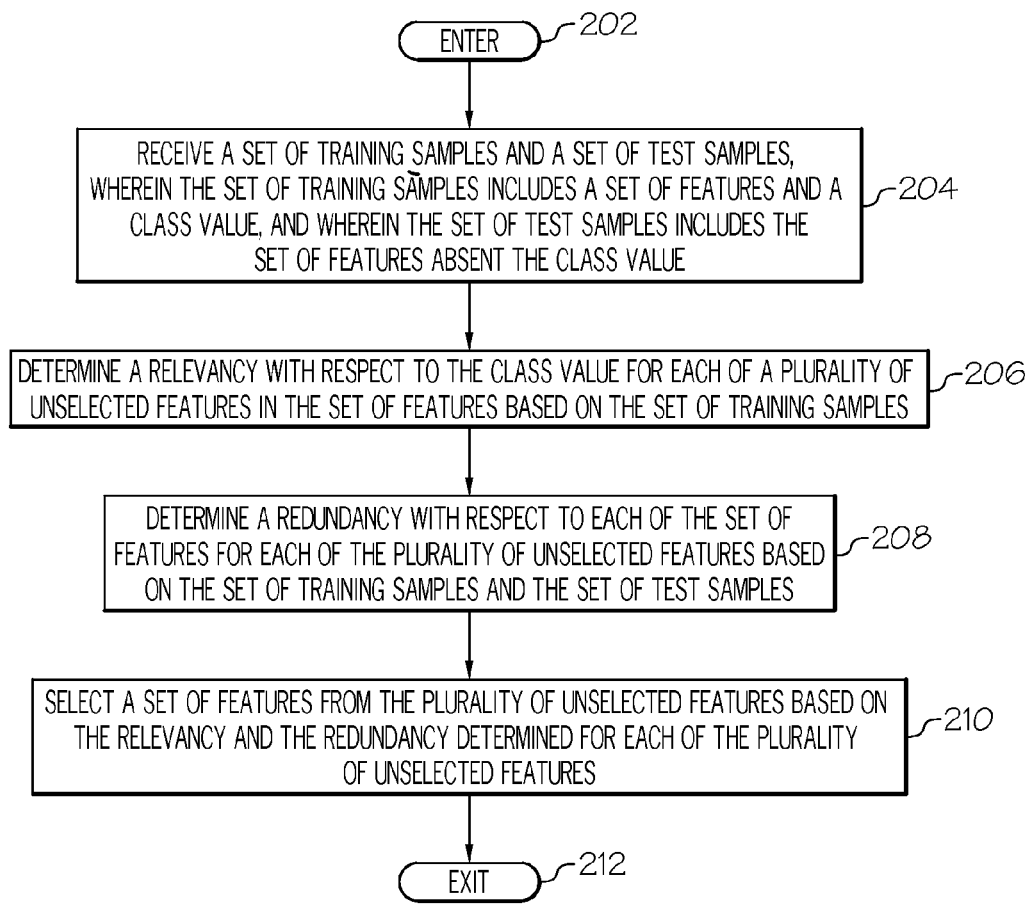
FIG. 2 is an operational flow diagram illustrating one example of a process for transductively selecting features from a feature space with Maximum-Relevancy and Minimum-Redundancy according to one embodiment of the present invention.

FIG. 2 is an operational flow diagram illustrating one example of a process for transductively selecting features from a feature space with Maximum-Relevancy and Minimum-Redundancy. The operational flow diagram begins at step 202 and flows directly to step 204. The feature selection module 109, at step 204, receives at least one training dataset and at least one test dataset. The at least one training dataset includes a first set of features and a class value. The at least one test dataset includes a second set of features absent a class value. The feature selection module 109, at step 206, determines a relevancy with respect to the class value for each of a plurality of unselected features in the first set of features. The feature selection module 109, at step 208, determines a redundancy with respect to each of the first set of features and the second set of features for each of the plurality of unselected features in the first set of features. The feature selection module 109, at step 210, selects a set of features from the plurality of unselected features based on the relevancy and the redundancy determined for each of the plurality of unselected features. The control flow exits at step 212.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention have been discussed above with reference to flowchart illustrations and/or block diagrams of methods, apparatus (systems) and computer program products according to various embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. An information processing system for selecting features from a feature space, the information processing system comprising:
a memory;
a processor communicatively coupled to the memory; and a feature selection module communicatively coupled to the memory and the processor, wherein the feature selection module is configured to perform a method comprising:
  obtaining, by a processor, a set of training samples and a set of test samples, wherein the set of training samples comprises a first set of features and a class value, and wherein the set of test samples comprises a second set of features, where the second set of features is the first set of features absent the class value;
  determining, for each of a plurality of unselected features in a plurality of features comprising the first and second set of features, a relevancy with respect to the class value based on the set of training samples;
  determining, for each of the plurality of unselected features, a redundancy with respect to the plurality of features based on both the set of training samples and the set of test samples;
  selecting a set of features from the plurality of unselected features based on the relevancy and the redundancy determined for each of the plurality of unselected features, wherein the selecting is performed based on;

$$\max_{x_j \in X - S_{m-1}} \left[ I(x_j^{training}; c^{training}) - \frac{1}{m-1} \sum_{x_i \in S_{m-1}} I(x_j^{training+test}; c^{training+test}) \right],$$

where $x_j$ is a jth feature that is sample independent, $x_{training}$ is a jth feature based on the set of training samples, $x_j^{training+test}$ is a jth based on the set of training samples and the set of test samples, i is an integer, X is a set of all features, $S_{m-1}$ is a set of m−1 features, c is the class value, and I is mutual information; and
  programming a processor to perform at least one of a set of classification operations and a set of regression operations based on the set of features that have been selected.

2. The information processing system of claim 1, wherein each of the set of features that has been selected has a maximum relevancy among each of the plurality of unselected features with respect to the class value based on the set of training samples, and has a minimum redundancy among each of the plurality of unselected features with respect to the set of features based on the set of training samples and the set of test samples.

3. The information processing system of claim 1, wherein the relevancy is determined based on mutual information between a given unselected feature in the plurality of unselected features and the class value based on the set of training samples.

4. The information processing system of claim 3, wherein the mutual information is determined based on comprising:
  determining that the class value is within a given threshold;
  rounding the class value; and
  multiplying the class value by a scalar, wherein an entropy of the class value after being multiplied by the scalar is within a given threshold of an original entropy of the class value.

5. The information processing system of claim 1, wherein the redundancy is determined based on mutual information between a given unselected feature in the plurality of unselected features and each feature in the plurality of features.

6. The information processing system of claim 5, wherein the method further comprises:
  storing a set of counts for each of a set of values used to determine the mutual information between the given unselected feature and the plurality of features; and
  determining the mutual information between the given unselected feature and the plurality of features based on the set of counts that has been stored.

7. A non-transitory computer program product for selecting features from a feature space, the computer program product comprising:
  a storage medium readable by a processing circuit and storing instructions for execution by the processing circuit for performing a method comprising:
    obtaining, by a processor, a set of training samples and a set of test samples, wherein the set of training samples comprises a first set of features and a class value, and wherein the set of test samples comprises a second set of features, where the second set of features is the first set of features absent the class value;
    determining, for each of a plurality of unselected features in a plurality of features comprising the first and second set of features, a relevancy with respect to the class value based on the set of training samples;
    determining, for each of the plurality of unselected features, a redundancy with respect to the plurality of features based on both the set of training samples and the set of test samples;
    selecting a set of features from the plurality of unselected features based on the relevancy and the redundancy determined for each of the plurality of unselected features, wherein the selecting is performed based on $$\max_{x_j \in X - S_{m-1}} \left[ I(x_j^{training}; c^{training}) - \frac{1}{m-1} \sum_{x_i \in S_{m-1}} I(x_j^{training+test}; c^{training+test}) \right],$$

where $x_j$ is a jth feature that is sample independent, $x_j^{training}$ is a jth feature based on the set of training samples, $x_j^{training+test}$ is a jth based on the set of training samples and the set of test samples, i is an integer, X is a set of all features, $S_{m-1}$ is a set of m−1 features, c is the class value, and I is mutual information; and
  programming a processor to perform at least one of a set of classification operations and a set of regression operations based on the set of features that have been selected.

8. The non-transitory computer program product of claim 7, wherein each of the set of features that has been selected has a maximum relevancy among each of the plurality of unselected features with respect to the class value based on the set of training samples, and has a minimum redundancy among each of the plurality of unselected features with respect to the set of features based on the set of training samples and the set of test samples.

9. The non-transitory computer program product of claim 7, wherein the relevancy is determined based on mutual information between a given unselected feature in the plurality of unselected features and the class value based on the set of training samples.

10. The non-transitory computer program product of claim 9, wherein the mutual information is determined based on comprising:
   determining that the class value is within a given threshold;
   rounding the class value; and
   multiplying the class value by a scalar, wherein an entropy of the class value after being multiplied by the scalar is within a given threshold of an original entropy of the class value.

11. The non-transitory computer program product of claim 7, wherein the redundancy is determined based on mutual information between a given unselected feature in the plurality of unselected features and each feature in the plurality of features.

12. The non-transitory computer program product of claim 11, wherein the method further comprises:
   storing a set of counts for each of a set of values used to determine the mutual information between the given unselected feature plurality of features; and
   determining the mutual information between the given unselected feature and the plurality of features based on the set of counts that has been stored.

* * * * *